United States Patent
Dodds et al.

(10) Patent No.: US 10,989,717 B1
(45) Date of Patent: Apr. 27, 2021

(54) OXIDATIVE STRESS BIOMARKERS TESTING IN ANIMALS

(71) Applicant: HEMOPET, Garden Grove, CA (US)

(72) Inventors: Winifred Jean Dodds, Santa Monica, CA (US); Denis Marc Callewaert, Metamora, MI (US)

(73) Assignee: HEMOPET, Garden Grove, CA (US)

( * ) Notice: Subject to any disclaimer, the term of this patent is extended or adjusted under 35 U.S.C. 154(b) by 0 days.

(21) Appl. No.: 17/114,156

(22) Filed: Dec. 7, 2020

Related U.S. Application Data

(60) Provisional application No. 62/953,049, filed on Dec. 23, 2019.

(51) Int. Cl.
*G01N 33/88* (2006.01)
*G01N 33/68* (2006.01)

(52) U.S. Cl.
CPC ... *G01N 33/6893* (2013.01); *G01N 2333/525* (2013.01); *G01N 2333/575* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 2003/0119064 A1* | 6/2003 | Valkirs | G01N 33/573 435/7.1 |
| 2005/0100979 A1* | 5/2005 | Power | C07K 16/40 435/25 |
| 2005/0249788 A1* | 11/2005 | Reynolds | A23K 20/30 424/442 |
| 2016/0202272 A1* | 7/2016 | Dahl | G01N 33/6893 436/501 |

FOREIGN PATENT DOCUMENTS

JP WO2005059566 A1 * 6/2005 ............. G01N 33/92

OTHER PUBLICATIONS

Yoshida et al., English Translation of WO2005059566A1, Oxidative stress marker and process for producing the same, Google patents translation, pp. 1-9. (Year: 2021).*
Torzewski et al., Animal Models of C-Reactive Protein, Hindawl Publishing Corporation, Mediators of Inflammation, vol. 2014, 2014, pp. 1-7. (Year: 2014).*
Van Der Vekiens et al., Human and equine cardiovascular endocrinology: beware to compare, Cardiovascular Endocrinology 2013, vol. 2, No. 4, pp. 67-76. (Year: 2013).*

* cited by examiner

*Primary Examiner* — Gary Counts
(74) *Attorney, Agent, or Firm* — Greenberg Traurig, LLP

(57) ABSTRACT

Diagnosing an oxidative stress (OS) in companion animals comprises screening a bodily fluid sample to detect the presence of an OS biomarker, selectively isoprostane and antioxidants, HODE, microRNAs, TAC, GSH, MDA, and TNF-alpha. The sample can be saliva.

18 Claims, No Drawings

OXIDATIVE STRESS BIOMARKERS TESTING IN ANIMALS

CROSS REFERENCE TO RELATED APPLICATION

This application claims the benefit of priority to U.S. Provisional Patent App. No. 62/953,049 for OXIDATIVE STRESS BIOMARKERS TESTING IN ANIMALS filed Dec. 23, 2019. The contents of that application are incorporated by reference in its entirety herein, and priority is claimed from that application.

BACKGROUND

The present disclosure is directed to cellular oxidative stress testing in companion animals.

In people and animals, cells in homeostatic equilibrium are in a state of oxidative balance, namely, when there are sufficient cellular antioxidants (both small molecule radical scavengers and enzymes such as catalase and superoxide dismutase) to avoid a buildup of excess free radicals (oxidizing agents). However, when levels of oxidizing agents exceed antioxidants, the condition is termed oxidative stress (OS). OS is now known to trigger inflammatory responses and to be an underlying cause of most chronic diseases.

Extensive investigations of OS and chronic tissue inflammatory responses have established that they are major underlying risk factors that play key roles in the etiology of a range of human (and animal) diseases, including rheumatoid arthritis, cancers, diabetes, obesity, periodontal disease, neurodegenerative disorders, and cardiovascular diseases. The development and progression of these chronic diseases is influenced by a range of environmental, dietary, and lifestyle factors, and specific dietary components, that— along with exercise and some nutraceuticals—can significantly impact OS and inflammation.

Chronic inflammation resulting from increased free radical formation in OS, also called reactive oxygen species (ROS), occurs when tissues or organs receive inflammatory "mediator" messages that cause them to react as though a "trigger" such as a pathogen is present. Rather than repairing themselves, these cells can remain in an ongoing state of inflammation that can wax and wane for prolonged periods. Tissues thus become deficient in antioxidant mediators, such as glutathione, cysteine, ascorbic acid and other radical scavenging vitamins, as well as superoxide dismutase, catalase and other antioxidant enzymes, and these deficiencies are strongly correlated with poor clinical outcomes. For mammals in good health, ~25% of oxygen intake gives rise to ROS, whereas this increases with age and poor health to as much as 75%.

When cells undergo damage due to OS and inflammation, the incidence and severity of infections, obesity cardiovascular disease and cancers increase. These damaged cells release molecules that can be used as biomarkers for OS and inflammation. Biomarkers of clinical relevance in people and pets include isoprostanes, malondialdehyde, and several cytokines including tumor necrosis factor (TNF), hydroxyoctadecadienoic acids (HODEs), as well as certain microRNAs. Elevated levels of these biomarkers in biofluids (including plasma, urine and/or saliva) can be used to evaluate oxidative status and can be addressed with diet and supplement changes to promote beneficial antioxidant effects. On the other hand, alternative biomarkers, such as glutathione, certain microRNAs, and some enzymes are indicative of a healthy antioxidant condition. Biomarkers can be analyzed assays periodically to assess the response and adjust lifestyle, nutritional and nutraceutical therapy, as needed.

Significant efforts have been made toward the dietary management of OS. In contrast to small molecule antioxidants (e.g. ascorbic acid) that can neutralize one ROS/ molecule, recent studies have focused on the development of functional foods, e.g. those containing natural Nrf-2 activators since the transcription factor Nrf-2 upregulates expression of multiple antioxidant enzymes including superoxide dismutase, catalase, glutathione transferases and glutathione reductase. A single molecule of one of these enzymes can neutralize a huge number of ROS. Significant amounts of antioxidant radical scavengers and/or Nrf-2 activators are ingredients in many functional foods and supplements such as: turmeric (*Curcuma longa*); and its relative, ginger (*Zingiber officiale*); chili peppers (*Capsicum annuum*); green tea (*Camellia sinensis*, which contains tannins and polyphenol catechins, and other teas); soybeans (*Glycine max*); tomatoes (*Solanum lycopersicum*, rich in lycopenes); grapes (not for pets); honey (not for infants or very young animals); cranberries (*Vaccinium macrocarpon*, contains pro-anthocyanidins); licorice (*Glycyrrhiza glabra*); garlic (*Allium sativum*, in moderation for pets); milk thistle (*Silybum marianum*); cabbages and broccoli.

Some Primary Oxidative Stress Biomarkers

Isoprostanes are a family of prostaglandin-like compounds produced by non-enzymatic ROS-catalyzed peroxidation of arachidonic acid. The concentration of isoprostanes in biological fluid is considered the "gold standard" for quantifying OS in vivo in humans and certain animals.

MicroRNAs are small non-coding RNA molecules found mostly in the cells of plants, animals and some viruses. MicroRNAs regulate phenotypic characteristics by silencing and post-transcriptional regulation of gene expression.

Reduced glutathione (GSH) plays two key roles in the maintenance of redox balance. First, GSH is a major intracellular radical scavenger that can react with and neutralize ROS thus preventing ROS-mediated damage to macromolecules such as proteins and DNA.

GSH is also a co-substrate for Glutathione-S-Transferases (GSTs), a superfamily of enzymes best known for their ability to catalyze the conjugation of the reduced form of glutathione (GSH) to foreign substrates for the purpose of detoxification. GSTs are found in plants, animals, fungi, and some bacteria. In vertebrates there are over 18 distinct cytosolic GSTs which are expressed most tissues, but especially in liver, kidney, heart, lung, and brain tissues. High levels of GST are associated with resistance to the apoptosis (cell death) induced by a range of substances, including chemotherapeutic agents. The levels of specific GST isoforms in urine and serum are indicators of hepatocyte and renal tubular injury in transplantation, toxicity and viral infections of humans and rodents.

The production of GSH is dependent on the enzyme glutathione reductase (GSR), and the expression of GSR, as well as multiple cytosolic GSTs and other antioxidant enzymes including superoxide dismutase are upregulated by the transcription factor Nrf-2. Therefore, while direct measurement of Nrf-2 activation by diet, nutraceuticals, etc. is extremely difficult, the levels of glutathione in biological fluids can serve as a surrogate biomarker for Nrf-2 activation.

Malondialdehyde (MDA) is a key byproduct of the peroxidation of polyunsaturated fatty acids. It is very reactive and forms adducts with macromolecules, thereby altering or eliminating their function. MDA and/or MDA adducts are well established biomarkers for OS. However some methods for the measurement of MDA, including the thiobarbituric acid reactive substance (TBARS) assay as it was traditionally performed do not provide consistent reliable results. Malondialdehyde is potentially mutagenic, and has been found in heated edible oils such as sunflower and palm oils. Corneas of human patients suffering from keratoconus and bullous keratopathy have increased levels of MDA, and this aldehyde also can be found in tissue sections of joints from human patients with osteoarthritis.

Tumor Necrosis Factor-Alpha (TNF-α), also called cachexin or cachectin, is a cell signaling protein involved in systemic inflammation and is one of the cytokines that play a primary role in the acute phase inflammatory response. It is produced chiefly by activated macrophages, although it can be produced by many other cell types such as CD4+ lymphocytes, natural killer (NK) cells, neutrophils, mast cells, eosinophils, and even neurons.

TNF is an endogenous pyrogen that can induce fever, apoptotic cell death, cachexia, inflammation, inhibit tumorigenesis and viral replication, and respond to sepsis via interleukin IL-1 and IL-6 producing cells. Dysregulation of TNF production has been implicated in a variety of human diseases such as Alzheimer's disease, cancer, depression, psoriasis and inflammatory bowel disease (IBD).

Hydroxyoctadecadienoic Acids (HODEs) are derived from the peroxidation of linoleic acid. The concentration of HODEs have been shown to be altered in humans suffering from periodontal disease, type-2 diabetes, rheumatoid arthritis, cataracts, Alzheimer's disease and hepatitis-B and -C, so that HODEs may serve as useful biomarkers for early detection of these conditions.

Other Biomarker Enzymes include: Sorbitol Dehydrogenase, a cytosolic enzyme that converts sorbitol, the sugar alcohol form of glucose, into fructose; and 5' Nucleotidase, which catalyzes the phosphorolytic cleavage of 5' nucleotides, and is considered a maturation marker for T- and B-cells.

Measuring Biomarkers of Oxidative Stress

Traditionally, cellular biomarkers are measured in the serum and/or urine from humans and animals. However, collecting these samples especially from children and smaller animal species presents with difficulty and causes unnecessary stress.

Neither canine whole blood-, serum-, nor urine-based isoprostane quantitations are accurate, linear and predictive as a marker for tissue oxidative stress in the canine species. Similarly, there are no published studies of measuring HODEs as a biomarker of OS in companion animals There is a need for another form of OS testing in companion animals, especially canines.

There is also a need for managing and treating elevated biomarkers of Oxidative Stress.

Treatments and preventive health measures can include applicable drugs, diets, supplements and exercise.

SUMMARY

According to the disclosure, measurement is affected in saliva.

Collection of saliva is noninvasive, painless, relatively inexpensive and convenient for the individual. Salivary testing of OS and/or inflammatory biomarkers can reveal the latent or pre-clinical form of developing OS.

There is a need to provide for practical and rapid screening or testing for OS to permit enhancement of the health of animals. Current methods and findings in humans and rodents measure OS biomarkers primarily in serum or urine. However, while one can measure OS biomarkers in healthy dog serum, neither serum nor urine has provided reliable quantitative and linear measurements in healthy dogs or especially in those with chronic diseases, where one would predict their elevation from tissue OS.

In accordance with this disclosure there is provided a diagnostic test system for OS stress assessment in animals, in particular companion animals, such as dogs, cats, rabbits, hamsters, and horses.

Saliva can be used as a diagnostic tool to assess the health or disease status of an animal. Saliva is easily collected, stored and shipped, and provides a non-invasive means of multiple or serial sampling for use as a diagnostic tool for a variety of conditions in animals.

The disclosure uses a species-specific test for companion animals such as dogs or cats, and other animal species, and the appropriate methods.

The disclosure is further described in detail.

DETAILED DESCRIPTION

Different biomarkers are described and different abbreviations below are as follows.

IsoP, isoprostane(s); AOX, antioxidant capacity; CRP, C-reactive protein; GSH, glutathione; MDA, malonaldehyde; NO, nitric oxide; TAC, total antioxidant capacity; transcription factor Nrf-2 (Nuclear factor erythroid 2-related factor 2), TNF-alpha, tumor necrosis factor-alpha, and 9- or 13-NODE (hydroxyoctadecadienoic acids).

Diagnostic Assessment. Several dozen methods have been reported for measuring biomarkers for OS, AOX, and inflammation and many have been employed in biomedical research that overwhelmingly supports OS and inflammation (INF) as major risk factors for multiple diseases.

However, with just two recent exceptions (CRP in blood, and the albumin/creatinine ratio in urine) tests for these risk factors have generally been restricted to people and rodents within research laboratories and/or clinical trials, and have not been available for the routine monitoring of human or animal health and wellness.

Most biomarkers, especially those for OS and AOX, are notoriously unstable, as the ex vivo reaction of air with biofluids during transit, storage and/or processing can cause very large artifactual values. Rapid analysis close to the site of sample collection, or rapid freezing and transport of samples on dry ice, has been essential in order to obtain more reliable results using serum or urine. This testing has not been developed for companion animal saliva, until the present disclosure.

The present disclosure relates to a panel of biomarkers of OS for animals, particularly companion animals and more particularly dogs, cats or horses using saliva that permits the rapid, non-invasive screening of an animal's health/wellness.

Biomarkers for AOX and TAC

The present disclosure relates to a test for TAC in animals, particularly companion animals and more particularly dogs, cats or horses using saliva that permits the rapid, non-invasive quantitative screening for TAC in the animal.

The Nrf-2 serum assay using GSH as a surrogate biomarker. While Nrf-2 activation can be evaluated using complex protocols in a research setting, Nrf-2 is not a suitable clinical biomarker, as clinical samples must be stored and analyzed under conditions to avoid denaturation and the complexity and cost of the analysis prohibits widespread application. Although a reliable quantitative test that correlates with Nrf-2 activation has yet to be developed for use in canine saliva, the concentration of GSH in blood samples from normal canines has been reported to be 0.128±0.01 mM.

The present disclosure relates to a test for GSH, the concentration of which is regulated by the transcription factor Nrf-2 for animals, particularly companion animals and more particularly dogs, cats or horses using saliva that permits the rapid, non-invasive quantitative screening of GSH.

Lipid peroxidation. One of the major outcomes of ROS-mediated injury to tissue is lipid peroxidation. However, as typically performed, assays for OS biomarkers suffer from a lack of specificity and multiple interferences. More recently, improved methods for quantifying specific oxidized lipids, including measurement of MDA and 9- and 13-HODEs, primarily in human plasma or urine, have been developed.

MDA is a widely recognized biomarker for lipid peroxidation. Although the standard TBARS methodology is subject to multiple interferences, a novel and more accurate assay for the specific quantification of MDA has recently been developed. Healthy canines have been reported to have serum MDA levels ranging from 1.00 to 1.77 µM.

The present disclosure relates to a test for MDA for animals, particularly companion animals and more particularly dogs, cats or horses using saliva that permits the rapid, non-invasive quantitative screening of MDA in the animal.

TNF-alpha is produced primarily by activated macrophages, and as an endogenous pyrogen, is able to induce fever and apoptotic cell death. It is a primary mediator of inflammatory responses. Levels of TNF-alpha in the serum of normal canines have been reported to range from 0-4 pg/mL.

The present disclosure relates to a test for levels of TNF-alpha for animals, particularly companion animals and more particularly dogs, cats or horses using saliva that permits the rapid, non-invasive quantitative screening for levels of and also serum TNF-alpha in the animal.

HODEs are unsaturated fatty acids derived from the essential fatty acid, linoleic acid, and its various isomers are generated by either enzymatic or free radical mediated oxidation. The present disclosure relates to a test for levels of 9- and/or 13-HODE for animals, particularly companion animals and more particularly dogs, using saliva that permits the rapid, non-invasive quantitative screening for levels of 9 and/or 13-HODE in the animal.

NO is produced in mammals by three isoforms of the enzyme nitric oxide synthase that are differentially expressed and regulated, and have many physiological and pathophysiological roles ranging from regulation of vascular tone to inflammation and cancer.

NO is highly reactive, with multiple byproducts produced in vivo, including peroxynitrate, nitrate and nitrite (collectively NOx). Sensitivity and normal range levels of NOx in the serum of normal dogs have been reported to range from 15.1-25.5 µM) and have been shown to be elevated by up to 1000-fold higher in infections or other inflammatory conditions.

Drugs or byproducts of digestion of certain foods containing high levels of nitrates will also contribute to the NO value obtained by this method.

Prior Studies in Canine Cancer Patients.

Canine patients with multicentric lymphoma, oral fibrosarcoma, mast cell tumor, malignant melanoma, appendicular osteosarcoma, nasal tumors and peripheral ameloblastoma were studied. Each group consisted of 6 patients; antioxidant biomarkers were measured in serum and whole blood, and were compared to those of 31 healthy dogs. The increase of antioxidant enzyme activities in the cancer group demonstrated the activation of antioxidant defense mechanisms in different canine cancer diseases.

The present disclosure relates to a test for levels of Total Antioxidant Capacity (TAC) and other biomarkers of OS and/or inflammation: GSH, MDA, TNF-Alpha, HODE, NO and isoprostane biomarkers for animals, particularly companion animals and more particularly dogs, cats or horses using saliva that permits the rapid, non-invasive quantitative screening for TAC, GSH, MDA, TNF-Alpha, HODE, NO and isoprostane in the animal.

| Measurements in Dog Serum on Various Diets | | | | |
|---|---|---|---|---|
| Dogs (n = 20/ group) | Diet Group | Glutathione (mM) | Total Antioxidant (mM Trolox Equivalents) | Total MDA (µM) |
| | Regular | | | |
| Pre | | 5.2 ± 0.7 | 10.7 ± 6.4 | 2.2 ± 1.8 |
| 2 Weeks | | 5.3 ± 0.9 | 8.9 ± 1.5 | 3.7 ± 0.8 |
| 4 Weeks | | 5.1 ± 0.8 | 8.3 ± 1.0 | 2.6 ± 0.9 |
| | Bean Mix | | | |
| Pre | | 5.1 ± 0.9 | 10.5 ± 5.8 | 1.8 ± 1.3 |
| 2 Weeks | | 4.9 ± 0.9 | 8.1 ± 2.3 | 3.6 ± 1.1 |
| 4 Weeks | | 4.7 ± 1.0 | 7.6 ± 1.7 | 2.4 ± 0.8 |
| | Light Diet | | | |
| Pre | | 5.3 ± 0.6 | 11.2 ± 2.6 | 2.4 ± 1.1 |
| 2 Weeks | | 5.8 ± 0.9 | 7.6 ± 1.2 | 3.4 ± 1.0 |
| 4 Weeks | | 5.9 ± 0.6 | 8.0 ± 1.7 | 2.4 ± 0.9 |

The isoprostanes are prostaglandin-like compounds formed in vivo from the free radical-catalyzed peroxidation of arachidonic acid without the direct action of cyclooxygenase (COX) enzymes. These compounds have been shown to be accurate markers ROS-mediated lipid peroxidation in both animal (rodent, pig) and human models of OS, and are many times more reliable than MDA.

The isomers of hydroxyoctadecadienoic acid (NODE) are metabolites of the essential fatty acid, linoleic acid. In addition to enzymatic pathways involving 12- and 15-lipoxygenase enzymes, they are generated by ROS-mediated peroxidation under conditions of OS.

But different biomarkers do not measure identical aspects of OS. In fact, research data have shown that isoprostane levels in biofluids like plasma and urine are expected to be the same or correlated.

The urinary Isoprostane immunoassays developed to date for human and rodent urine either require costly and complex extraction protocols prior to analysis or contain specially formulated buffers. However, accurate quantitative measurement of isoprostanes in canine saliva has not been possible until the present disclosure.

Assays for quantitating hydroxyoctadecadienoic acids and microRNA have not yet been developed for clinical use in companion animal species until the present disclosure.

Biomedical tools for the analysis of OS are disclosed. They are indicative and correlate to markers of inflammation, and two of the important risk factors that play key roles in the development of a wide range of illness, including cancer, tissue inflammation, infections, periodontal disease, obesity, diabetes and neurodegeneration.

The disclosure provides a straightforward, reliable assay for OS biomarkers and for antioxidant capacity of biological fluids.

The present disclosure relates to a test for levels of oxidized lipid biomarkers, selectively isoprostanes, 9- and/or 13-HODE, microRNAs and other biomarkers for animals, particularly companion animals and more particularly dogs, cats or horses using saliva that permits the rapid, accurate, non-invasive quantitative screening for biolipids, selectively in the animal.

The saliva-based test assay quantifies the $15\text{-}F_{2t}$-isoprostane, 9- and/or 13-HODE and microRNA levels in dog saliva to determine if the pet's body is undergoing harmful OS. OS creates reactive oxygen species (ROS) causing cells to undergo damage and release biomarker lipids and enzymes that lead to tissue inflammation, infections, periodontal disease, obesity and even cancers. However, free radicals themselves are so reactive and short-lived that direct measurement is not possible. Thus, $15\text{-}F_{2t}$-isoprostane and 9 and/or 13-HODE levels serve as reliable surrogate biomarkers for the presence of ROS.

The saliva-based tests of this disclosure are novel isoprostane, HODE and microRNA tests, and are examples of a set of unique biomarker tests for pets that can be measured in saliva.

Biomarkers of clinical interest in people and pets include isoprostane, PGF2alpha, HODE, micro RNAs, MDA, TAC and others.

For quantitative testing, an animal's serum or saliva or other bodily fluid is added to the ELISA microtiter plate or other immunoassay platforms such as but not limited to lateral flow, or latex or bead agglutination, and the concentration(s) obtained therefrom are used as surrogate biomarkers for cellular oxidative stress.

Once collected at or received by the lab, the blood serum or saliva or other bodily fluid sample is then screened as possible using the ELISA method or other immunoassay platforms such as but not limited to lateral flow, or latex or bead agglutination, which measures the presence of OS.

Forms of bodily biological fluid, other than saliva, for instance urine, tears, sweat, or milk or other mucosal secretions can be used.

The detection of cellular oxidative stress can be performed with an immunoassay. Immunoassays include, but are not limited to, ELISA test, RIA test, latex agglutination, lateral flow immunoassay (LFIA), and beads. A preferable immunoassay is the ELISA test. Other immunoassays can be used and the choice of immunoassay can be determined by one of ordinary skill in the art.

A multitude of laboratory tests for analytes of interest are performed on biological samples for diagnosis, screening, disease staging, forensic analysis, drug testing, and other reasons. While a few qualitative tests have been reduced to simple kits for home use, the majority of quantitative tests still require the expertise of trained technicians in a laboratory setting using sophisticated instruments.

Optical means for detecting the binding of an analyte to a receptor is employed, or alternatively there can be electrochemical detection, in which binding of an analyte directly or indirectly causes a change in the activity of an electroactive species adjacent to an electrode.

Therefore, there exists within the field of analyte sensing, and in particular for applications in which analytes must be determined within biological samples such as blood, saliva or urine, a need for apparatus that can rapidly and simply determine analytes at a point of service (P-O-S), and can be performed by less highly trained staff than is possible for conventional laboratory-based testing. It would be of benefit in the diagnosis and treatment of critical veterinary conditions for the veterinarian or veterinary technician to be able to obtain clinical test results without delay. The apparatus should be adaptable to determination of a range of analytes and capable of single-use so that there can be disposal of the sample after testing.

A device according to the present disclosure has the advantage that the sample and a second fluid can contact the sensor array at different times during an assay sequence. The sample and second fluid may also be independently formed with other reagents or compounds present initially as dry coatings within the respective conduits. Controlled motion of the liquids within the device further permits more than one substance to be added into each liquid whenever the sample or fluid is moved to a new region of the conduit.

In operation, an amount of a preferable biological sample is placed into the designated sample area or chamber of a device. The applied sample area or device can have reading zones or the area or device can be placed into a reading apparatus. A metered portion of the sample can be amended with at least one conjugate, and is then contacted with the immunosensor. A second fluid, which contains an inactive substrate for the analyte of interest, is used to rinse the immunosensor substantially free of unbound conjugate, and the response of the immunosensor is recorded and analyzed for the presence, or amount of, analyte of interest. The applied sample area or device may contain a plurality of immunosensors and reagents.

After the reading, the operator removes and discards the applied sample area or device. The reader is then ready for another measurement. While the use of the disclosure is frequently referred to in a biological or medical context, it will be appreciated that the present disclosure may be practiced in any situation where it is desired to perform in situ chemical analyses of liquid samples at speeds which approach real-time.

A dipstick test device can be used for detecting an analyte in a liquid sample such as saliva or other biological fluid by treating the analyte with at least one liquid reagent to form a detectable reaction product. The device can include a) an aqueous impermeable, aqueous insoluble reaction zone, adapted to retain the detectable reaction product; and b) a control absorbent above, and in liquid-transferring relation with, the reaction zone. The control absorbent can have predetermined, limited liquid-absorbing capacity, and the dipstick is configured for location with a vessel containing the sample. The control absorbent is above the reaction zone, so that the control absorbent fills with sample and the reaction zone incubates with the sample. The device may further include an absorbent reservoir which can move into liquid transferring contact with the reaction zone.

This device and method is for use for detecting an analyte, for example, using an immunoassay. An analyte in a sample may be detected by treating the sample with various reagents, such as labeled immunological binding partners to the analyte and reagents to enable detection of the label. Often, the sample is washed between administrations of various reagents.

An assay may depend on controlling the amount of reactants exposed to the sample and the duration of the reactions taking place. It is desirable to have the ability to assay small sample volumes with relative low concentrations of analyte, and/or to detect relatively small differentials in analyte concentration. Finally, it is desirable to have a system to permit measuring whole blood samples, serum and saliva or other bodily fluid without complex equipment.

One method for adding and washing reagents in an immunoassay uses an absorbent material to move liquid washes and reagents through a solid substrate such as a membrane to which other reactants are immobilized.

There can be an immunoassay test device including sorbent material for drawing liquid through a microporous membrane at the bottom of a test well. The sorbent material is resiliently biased away from the membrane, and it draws liquid through the membrane only when the two are forced together to overcome the bias. Sorbent material comprises a surface layer which is hydrophobic and a bulk portion which is wettable. Reagents are added serially to the test well and, after each reagent has been in the well for a prescribed time, the membrane and sorbent material are forced together to draw off liquid before the next reagent is added.

Generally there is a dipstick test device for detecting an analyte in a liquid sample such as saliva or other biological fluid by treating the analyte with at least one liquid reagent to form a detectable reaction product. The test device includes two components: a) means defining an aqueous permeable, aqueous insoluble reaction zone, adapted to retain the detectable reaction product; and, integral with or separate from the reaction zone, b) a control absorbent above, and in liquid-transferring relation with, the means defining a reaction zone. The control absorbent has a predetermined, limited, liquid-absorbing capacity. The dipstick is sized and configured for insertion in a vessel containing the sample, with the control absorbent oriented above the means defining a reaction zone, so that the control absorbent fills to capacity and the means defining a reaction zone incubates with the sample.

The reaction zone comprises at least one reactant e.g. a specific binding partner for the analyte participating in a reaction to form the detectable product.

The reaction product is detected by visual inspection, and the means defining a reaction zone is visible by external inspection of the device; optionally, the device includes a contrast region surrounding the reaction zone to aid in the assay by contrasting with the reaction zone in respect to a characteristic being assayed; also optionally, the device can include an intensity scale for quantitative detection of sample analyte.

The reaction zone is either integral with the control absorbent or it is attached to a face of the control absorbent. The reaction zone can define at least two reaction regions, and the test device comprises means for isolating the reaction regions from each other. At least one reaction region may be a control region.

The device includes an aqueous impermeable face plate having at least one opening to allow liquid to reach the means defining a reaction zone. In order to provide a flush test head, the means defining a reaction zone comprises a flat reagent retention element having a node positioned to extend into each face plate opening.

The test may include a reagent pack sized and configured to supply a plurality of reagents to the reaction zone. For example, the reagent pack may include liquid reagents for generating a detectable reaction product.

The reaction zone can be positioned at one end of an elongated dipstick, and the device further can comprise a filter assembly positioned at an end of the dipstick. The device can include a reaction tray comprising a well for the filter assembly on the dipstick and to retain the filter assembly as the dipstick is removed from the well.

Detecting an analyte in a sample is by reacting the analyte with at least one reagent to form a detectable reaction product. The method can include:

a) providing a test device comprising a control absorbent above, and in-transferring relation with, a defined a reaction zone, the control absorbent having a predetermined, limited, liquid-absorbing capacity; the control absorbent is in liquid-transferring relationship with the defined reaction zone;

b) inserting the dipstick into a vessel containing a predetermined volume of sample, with the control absorbent oriented above the defined reaction zone;

c) incubating the predetermined sample volume with the reaction zone;

d) allowing formation of the detectable reaction product; and e) detecting the reaction product.

A method for diagnosing OS in a dog or other companion animal comprises the steps of collecting a sample of saliva; screening the sample to detect a level of at least one of a number of OS markers and detecting and diagnosing the presence of OS based on the level of one or more markers.

A method for diagnosing OS in a dog or other companion animal comprises the steps of collecting a sample of saliva; screening the sample to detect a level of at least one isoprostane, and detecting and diagnosing the presence of OS based on the quantitative level of the isoprostane.

A method for diagnosing OS in a dog or other companion animal comprises the steps of collecting a sample of saliva; screening the sample to detect a level of at least one HODE, and detecting and diagnosing the presence of OS based on the quantitative level of the HODE.

The method further comprises collecting a first testing portion of the saliva sample and wherein the first testing portion is the sample for use in the screening step. [Glucuronidase pretreatment is not required for saliva samples.]

The method includes collecting a sample of about 1-3 milliliters.

The method includes the screening step utilizes an enzyme-linked immunosorbent assay (ELISA) testing system to detect the level of the saliva-based OS marker.

The method of the disclosure is such that, for example, a level of OS isoprostane marker above 1.75 ng/mL in saliva is indicative of OS.

The method of the disclosure is such that, for example, a level of OS isoprostane marker less than 1.75 ng/mL in saliva is indicative of a normal level of OS for canine species.

The method of the disclosure is such that, for example, a level of OS HODE marker above 0.31 ng/mL in saliva is indicative of OS.

The method of the disclosure is such that, for example, a level of OS HODE marker between 0.26-0.75 ng/mL in saliva is indicative of a normal level of OS.

Results

After completing the initial clinical trial studies, analyzing 282 clinical patient samples; 79 of them (35%) were positive, having isoprostane levels, for example, above the normal reference range we have established (i. e., 0.5-1.75 ng/mL of saliva).

Of the 79 dogs testing positive, there were: 34% spayed females, 32% neutered males, 21% intact males and 15% intact females. The ages ranged from 4 months to 15 years, although most were middle aged or older. The weight range was 4-143 pounds, with 84% being medium to large or giant in size; no breed type predominated.

The diets fed the 79 positive dogs included: 40% ate only a commercial raw diet; 20% only a commercial dry kibble; 13% a home cooked or home prepared raw diet, and 3% ate a combination of a commercial kibble and raw.

Of the 79 positive dogs, 38 also had saliva-based profiles run for food sensitivity and intolerances to 24 foods. Interestingly, only 3 of these 38 dogs had Saliva based test results that were reactive (20 or more foods). These results suggest that dogs with clinical issues related to intense itching, scratching, chewing, and bowel irritability had relatively few identified foods as the culprits. Environmental exposure to inhalants, fleas, ticks, mites and other insects as well as contact reactants could be involved; and 3 dogs were taking an isooxazoline parasiticide. See Summary Table below.

| Parameter | % | % | % | % |
|---|---|---|---|---|
| Pet Size (weight) | Small 22 | Medium 41 | Large/Giant 43 | — |
| Pet Age (yrs) | <2 12 | 2-4 21 | 4-10 45 | >10 24 |
| Pet Sex | Male 21 | MN 32 | Female 15 | FS 34 |
| Pet Diet | Only Raw 40 | Only Dry Kibble 20 | Kibble + Raw Combo 3 | Homemade Cooked or Raw 13 |

The sex breakdown and ages could merely reflect increased choice of testing as older pets are more likely to be neutered or spayed and have some health issues.

Positive testing dogs should be retested in about 6 months after being on foods and supplements designed to lower their OS. The beneficial outcome of 50 dogs which initially tested positive for elevated isoprostanes revealed reduced isoprostane levels when retested 5-6 months after taking the supplements listed below.

Positive Results
  Isoprostane level was positive in different dogs.
  Of 79 Positives:
  43% ate commercial Raw (sole or as a combo)
  20% are only commercial dry Kibble
  0.25% ate home prepared cooked or raw diets
  The rest ate a variety of foods.

The list below includes supplements that can help reduce this level, and patients were retested again after about 6 months to see if the isoprostane level is waning.

The saliva based test is a novel isoprostane test, and is a unique biomarker test for pets that is measured quantitatively in dog saliva.

Negative Results
  Isoprostane (i.e. in the saliva-based test) result was normal (less than 1.75 ng/mL)

Outcomes Summary for 50 Positive Cases after 5-6 months on Supplements

| Cases | Isoprostane Before Supplements (ng/mL) | Isoprostane 5-6 months After Supplements (ng/ml) | Clinical Comments |
|---|---|---|---|
| 1 | 2.13 | 2.0 | Cancer risk |
| 2 | 2.9 | 1.75 | Improved respirations |
| 3 | 1.92 | 0.9 | Reduced scratching/itching |
| 4 | 1.76 | 1.1 | Thyroid function improved |
| 5 | 2.3 | 1.85 | Hemangiosarcoma risk |
| 6 | 1.9 | 0.7 | No more urinary tract infections |
| 7 | 3.2 | 2.1 | Improved agility performance |
| 8 | 1.8 | 1.85 | No change |
| 9 | 2.3 | 1.6 | Mammary carcinoma removed |
| 10 | 1.95 | 1.4 | Less foot itching/tear staining |
| 11 | 2.26 | 1.73 | Gut issues mostly resolved |
| 12 | 2.6 | 1.8 | Allergy issues reduced |
| 13 | 1.89 | 0.8 | Dermatitis issues improved |
| 14 | 1.94 | 0.9 | Itchy feet better; likes cool floor |
| 15 | 2.4 | 1.95 | Still healthy |
| 16 | 1.83 | 1.55 | Itchy pimples are clearing |
| 17 | 1.9 | 1.85 | Still healthy |
| 18 | 2.5 | 2.4 | Has microvascular dysplasia |
| 19 | 1.95 | 1.93 | On raw diet, healthy |
| 20 | 2.0 | 0.83 | Severe skin/ear itching better |
| 21 | 3.0 | 2.0 | Licks hind paws; improving |
| 22 | 2.95 | 2.45 | Recurring gut, skin, ear issues |
| 23 | 1.8 | 0.6 | Itching less |
| 24 | 1.78 | 1.1 | Scabby skin, improving |
| 25 | 2.75 | 1.15 | Severe itching; diet related |
| 26 | 3.25 | 2.25 | Itching/biting feet, improving |
| 27 | 2.45 | 2.3 | Scabby ears/skin, may be less |
| 28 | 2.55 | 2.6 | IBD, not food related |
| 29 | 1.76 | 0.6 | On isoxazoline preventive |
| 30 | 1.95 | 1.27 | Behavior issues improved |
| 31 | 2.50 | 1.5 | Severe coat loss, improving |
| 32 | 2.0 | 0.55 | Recurring ear fungus, improved |
| 33 | 3.2 | 2.7 | Sluggish, bloody stool, better |
| 34 | 1.8 | 1.4 | Seizures lessened |
| 35 | 3.8 | 2.3 | Raw diet, beef reactive, better |
| 36 | 2.3 | 1.8 | Cardiomyopathy improved |
| 37 | 3.2 | 2.8 | Chronic scratching/hives, better |
| 38 | 3.15 | 2.75 | Itching/licking improved |
| 39 | 2.9 | 1.94 | Itching/licking improved |
| 40 | 2.75 | 2.7 | Still healthy, intact female |
| 41 | 1.85 | 1.77 | Raw diet, still healthy |
| 42 | 1.92 | 1.84 | Raw diet, still healthy |
| 43 | 3.6 | 2.15 | Chronic gut issues improved |
| 44 | 2.75 | 2.33 | Food intolerances remain |
| 45 | 1.76 | 0.65 | Mild cardiomyopathy resolved |
| 46 | 2.15 | 1.63 | Strong food intolerance, better |
| 47 | 1.77 | 1.75 | Still healthy |
| 48 | 2.6 | 2.11 | Raw diet, still healthy |
| 49 | 1.97 | 1.88 | Strong chicken sensitivity |
| 50 | 3.40 | 2.05 | Very itchy, improving |
| Total | Mean 2.32 ± 0.546 | Mean 1.73 ± 0.615 | Favorable overall |

GENERAL

Many different formats are possible for carrying the sample bodily fluid to the reaction zone. In some cases the bodily fluid is applied to an appropriate filter paper or other carrier material and the filter paper or other carrier material with that fluid sample is impregnated on and in the paper or other carrier material carrier and is either applied at a testing laboratory or sent to a laboratory by any convenient means for analysis. The paper or other carrier material including the sample may, for instance, in one part contain saliva or other bodily fluid, and in another separate part there can be serum or urine. By using filter paper or other carrier material as the carrier, it can be easy for an owner of a pet to simply mail a sample to a laboratory for appropriate testing of one or more biomarkers. The filter paper or other carrier material can have one or more reaction zones for different biomarkers. This carrier system of filter paper or other carrier material permits for a wholly or partly dehydrated sample to be carried to a laboratory for subsequent processing, which can include a hydration step prior to analysis in an appropriate analyzer.

In the specification, there have been disclosed typical embodiments of the disclosure. Although specific terms are employed, they are used in a generic and descriptive sense only and not for purposes of limitation, the scope of the disclosure being set out in the claims. It is therefore to be understood that within the scope of the appended claims the disclosure may be practiced otherwise than as described.

The invention claimed is:

1. A method for diagnosing and treating oxidative stress (OS) in a dog comprising the steps of screening a saliva sample of a dog to detect a level of at least an isoprostane OS biomarker; detecting the presence of the isoprostane biomarker based on a quantitative level of the isoprostane OS biomarker, and diagnosing OS in the dog based on an increased quantitative level of the OS isoprostane biomarker, and treating a diagnosed level above 1.75 ng/ml of the isoprostane OS biomarker with nutritional supplements for about six months to lower the level below 1.75 ng/ml.

2. The method of claim 1 wherein a level of an OS isoprostane above 1.75 ng/mL in saliva is indicative of increased OS in the dog.

3. The method of claim 1 wherein a level of an OS isoprostane between 0.5-1.75 ng/mL in saliva is indicative of a normal level of OS in the dog.

4. A method for diagnosing and treating oxidative stress (OS) in a dog comprising the steps of screening a saliva sample of of a dog to detect a level of an isoprostane and a HODE derived from peroxidation of linoleic acid, detecting the presence of OS based on the quantitative level, diagnosing the oxidative stress in the dog based on an increased quantitative level of the isoprostane and the HODE OS biomarkers and treating a diagnosed level above 1.75 ng/ml of the isoprostane OS biomarker with nutritional supplements for about six months to lower the level below 1.75 ng/ml.

5. The method of claim 4 comprises screening the levels of both the isoprostane and the HODE, detecting the presence of the OS based on the quantitative level, and diagnosing the oxidative stress in the dog based the quantitative level of both the isoprostane or the HODE.

6. The method of claim 4 wherein a level of isoprostane above 1.75 ng/mL in saliva is indicative of increased OS stress in the dog.

7. The method of claim 4 wherein a level of isoprostane between 0.5-1.75 ng/mL in saliva is indicative of a normal level of OS stress in the dog.

8. The method of claim 5 wherein a level of isoprostane above 1.75 ng/mL in saliva is indicative of increased OS stress in the dog.

9. The method of claim 5 wherein a level of isoprostane between 0.5-1.75 ng/mL in saliva is indicative of a normal level of OS stress in the dog.

10. A method for diagnosing and treating oxidative stress (OS) in a dog comprising the steps of screening a saliva sample of a dog to detect of at least an HODE OS biomarker derived from peroxidation of linoleic acid, detecting the presence of OS based on the quantitative level of the HODE OS biomarker, diagnosing the oxidative stress in the dog based on an increased quantitative level of the HODE OS biomarker, and treating a diagnosed level above 0.31 ng/ml of the HODE OS biomarker with nutritional supplements to lower the level.

11. The method of claim 10 wherein a level of the HODE above 0.31 ng/mL in saliva is indicative of increased OS stress in the dog.

12. The method of claim 10 wherein a level of the HODE between 0.26-0.75 ng/mL in saliva is indicative of a normal level of OS stress in the dog.

13. The method of claim 1 wherein a level of the OS isoprostane above 1.75 ng/mL in saliva is indicative of increased OS in the dog, and wherein a level of an OS isoprostane between 0.5-1.75 ng/mL in saliva is indicative of a normal level of OS in the dog.

14. The method of claim 10 wherein a level of the HODE above 0.31 ng/mL in saliva is indicative of increased OS stress in the dog, and wherein a level of HODE between 0.26-0.75 ng/mL in saliva is indicative of a normal level of OS stress in the dog.

15. The method of claim 1 wherein the nutritional supplements include turmeric and green tea.

16. The method of claim 4 wherein the nutritional supplements include turmeric and green tea.

17. The method of claim 10 wherein the nutritional supplements include turmeric and green tea.

18. A method for diagnosing and treating oxidative stress (OS) in a dog comprising the steps of screening a saliva sample a dog to detect a level of at least an isoprostane OS biomarker; detecting the presence of the isoprostane OS biomarker based on a quantitative level of the isoprostane OS biomarker, and diagnosing OS in the dog based an increased quantitative level of the isoprostane OS biomarker, and treating an increased level of the isoprostane OS biomarker indicative of OS when diagnosed to be above 1.75 ng/ml indicative of OS with nutritional supplements including turmeric and green tea.

* * * * *